United States Patent [19]
Kuzyk

[11] Patent Number: 5,779,974
[45] Date of Patent: Jul. 14, 1998

[54] FROZEN PLASMA THAWING SYSTEM

[76] Inventor: Roman Kuzyk, 110 Sewell Ave., Trenton, N.J. 08610

[21] Appl. No.: 550,291

[22] Filed: Oct. 30, 1995

[51] Int. Cl.⁶ .................................................. A61M 1/14
[52] U.S. Cl. .................... 422/44; 165/104.31; 422/309; 604/903
[58] Field of Search .................. 422/1, 40, 41, 422/44, 307, 309; 604/903; 165/80.5, 104.28, 104.31

[56] References Cited

U.S. PATENT DOCUMENTS

| | | | |
|---|---|---|---|
| 3,441,479 | 4/1969 | Jankay | 422/44 X |
| 4,486,389 | 12/1984 | Darnell et al. | 422/307 |
| 4,852,641 | 8/1989 | Noble | 165/80.1 |
| 4,874,033 | 10/1989 | Chatelain et al. | 165/1 |
| 5,243,833 | 9/1993 | Coelho et al. | 62/376 |
| 5,364,385 | 11/1994 | Harms et al. | 604/410 |

*Primary Examiner*—Krisanne M. Thornton
*Attorney, Agent, or Firm*—Longacre & White

[57] ABSTRACT

A technique and apparatus for rapidly thawing a frozen blood plasma unit. The holder maintains a plasma unit pouch submerged in a manner which affords substantial thermal contact between the plasma unit and the fluid bath. The fluid is manipulated to provide a kneading effect on the exterior surface of the bag to enhance thawing efficiency.

7 Claims, 4 Drawing Sheets

FIG. 1
PRIOR ART
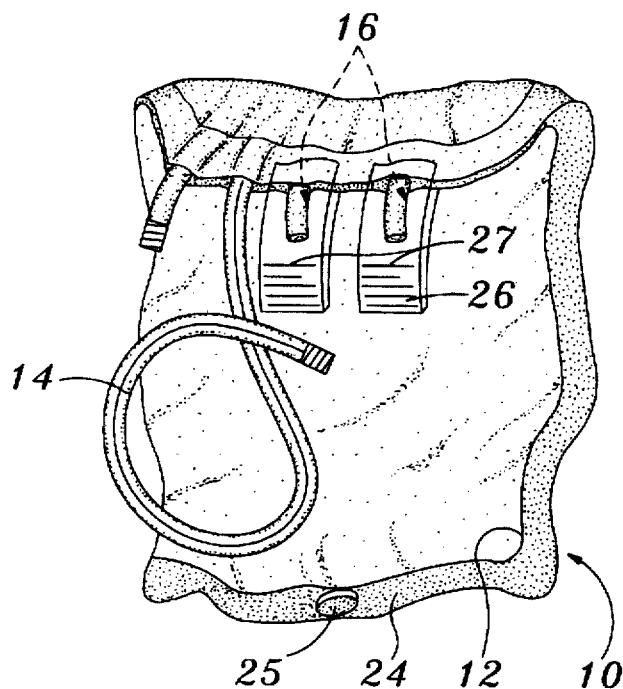
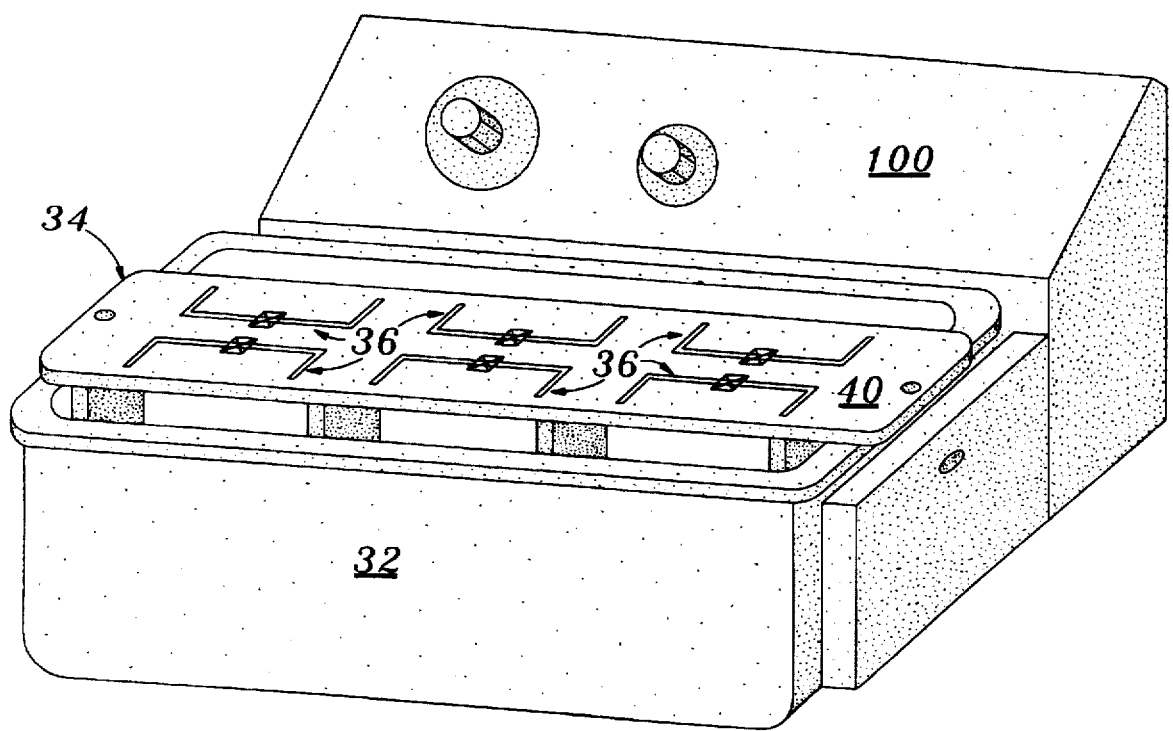
FIG. 2

FROZEN PLASMA THAWING SYSTEM

BACKGROUND FOR THE INVENTION a) Field of the Invention

This invention relates to improvements in the thawing of frozen blood and/or blood plasma units. Storing blood plasma in a frozen state and then thawing it when needed is a common practice in blood banks of hospitals and the like.

b) Description of Related Art

For many years the typical practice in the blood bank has been to select the required unit of blood and/or plasma and simply place it into a controlled temperature water bath to thaw the unit to the liquid state. Sometimes this thawing procedure includes some form of secondary agitation of the bag or blood unit. After thawing, the unit is removed from the water bath and is temperature controlled for use anytime during the next twenty-four hours.

Blood and/or plasma units typically are in the form of a sealed, prepackaged plastic pouch, holding 250 milliliters or so of plasma or blood product. The pouch includes one or more connector tubes through which the product may flow when the unit is in use. The connector tubes typically are presealed with a plastic membrane which is punctured when the unit is connected to the delivery catheter, as by a needle set inserted into the tube to puncture the membrane.

U.S. Pat. No. 4,486,389 discloses a technique and system which achieves thawing in a water bath, while maintaining the plasma bag in a dry, contaminant-free configuration, wherein the frozen plasma unit is placed within a thin, open-topped plastic bag. The bag then is placed in a special holder associated with the water bath. The holder and the bag cooperate to maintain the plasma unit, which is within the lower end of the thin plastic bag, well submerged below the surface of the water. The thin, open topped plastic bag conforms closely to the shape and configuration of the frozen plasma container thereby avoiding any substantial insulative spaces which might retard the thawing process. The holder and water bath are specially constructed to facilitate easy attachment and detachment of the bag from the holder. After the thawing process has been completed, the plastic bag is removed in its entirety and the still dry, thawed plasma unit maybe removed with assurance that it has not been contaminated by bacteria as a result of contact with the thawing bath.

While prior techniques and apparatus variously disclosed provides improvement over conventional systems for thawing frozen plasma, the need still exists for a more rapid and effective thawing technique. In many instances where thawing of plasma is required, time is of the essence, and may, in fact, save lives. Therefore, the need exists for a frozen plasma thawing system having improved efficiency and reduced thawing time.

SUMMARY OF THE INVENTION

It is among the objects of the invention to provide an improved system for thawing frozen blood and/or plasma units.

Another object of the invention is to provide a system of the type in which the thawing time is significantly decreased.

A further object of the invention is to provide improved, yet simplified apparatus for practicing the invention.

The present invention achieves the aforementioned objectives by providing a technique and system which simulates a kneading effect whereby reduced thawing time is achieved.

The present invention provides a significant improvement and reduction in thaw time by creating a forced and directed concentration of fluid by rocking the fluid bath and forcing the fluid through ports in a mid-bath baffle and directing the fluid against the object(s) being thawed.

BRIEF DESCRIPTION OF THE DRAWINGS

The foregoing and other objects and advantages of the invention will be appreciated more fully from the following further description thereof, and with reference to the accompanying drawings wherein;

FIG. 1 is an illustration of a typical frozen plasma unit pouch for insertion into the thaw bath;

FIG. 2 is a perspective view of one embodiment of the apparatus of the invention comprising a plasma bath unit and a control unit;

DESCRIPTION OF THE PREFERRED EMBODIMENT

Figure 3A:
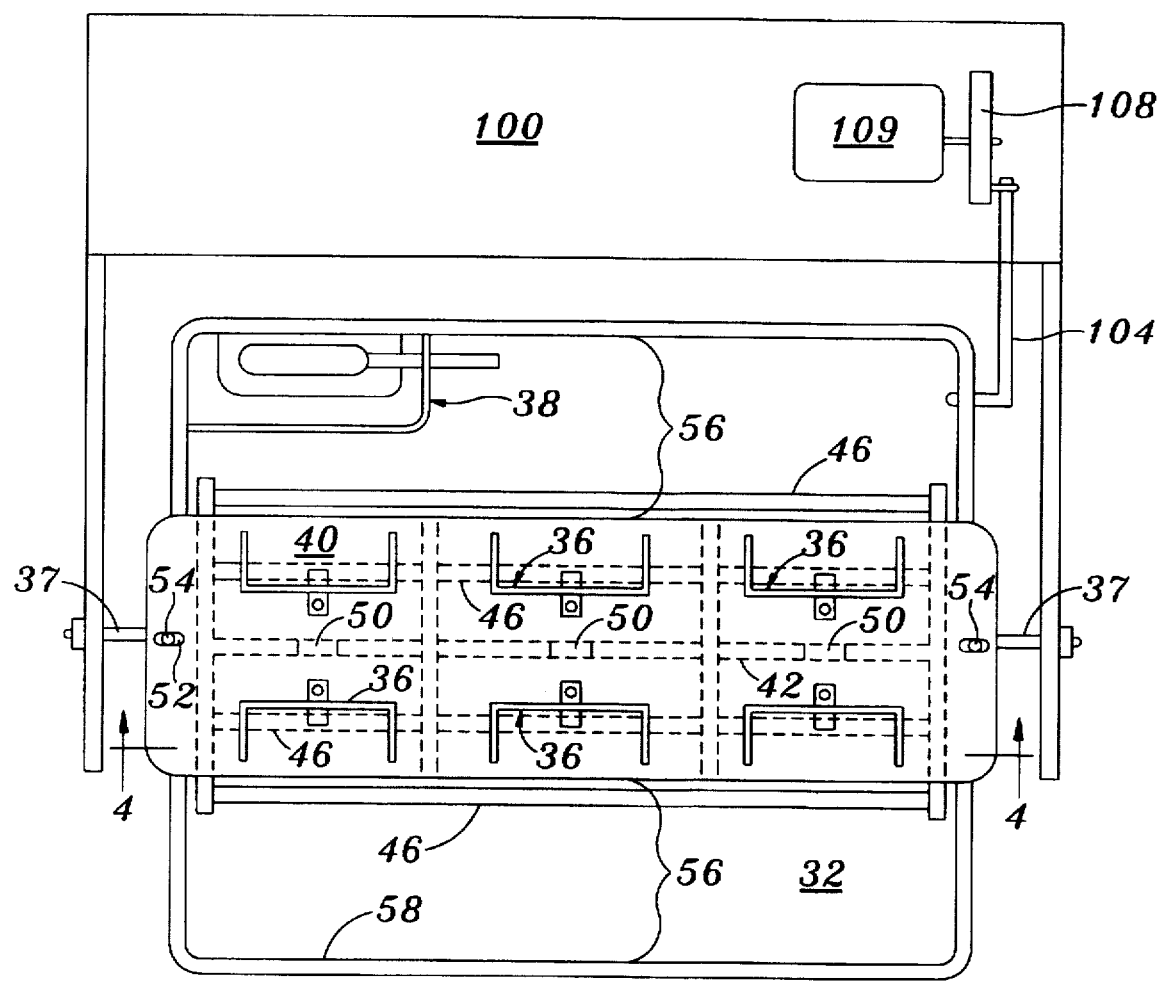
FIG. 3a is a plan view of one embodiment of the invention illustrating the fluid bath, a bag holder and control unit.
Figure 4:
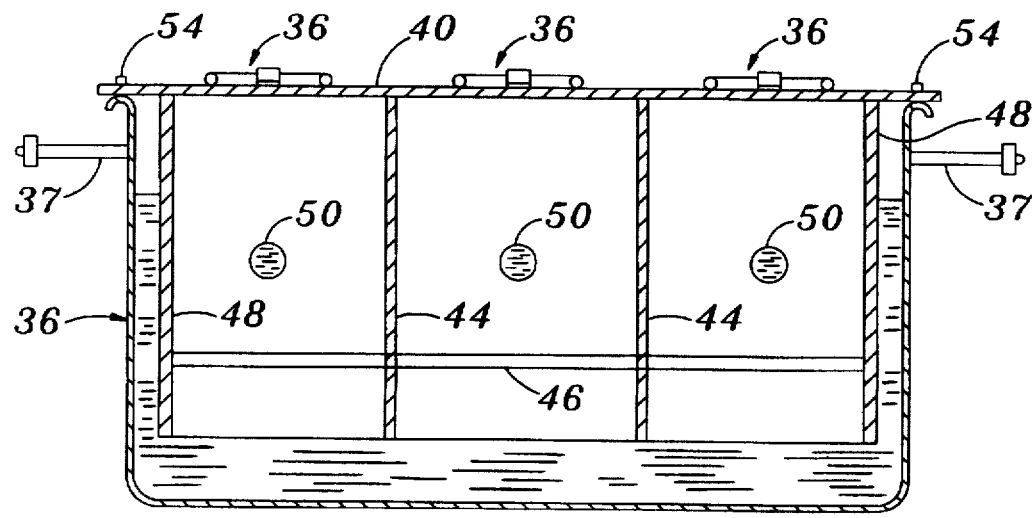
FIG. 4 is an illustration of the system of FIG. 3 as seen along the line 4—4 and showing the submerged portion of the fluid bath.
Figure 3B:
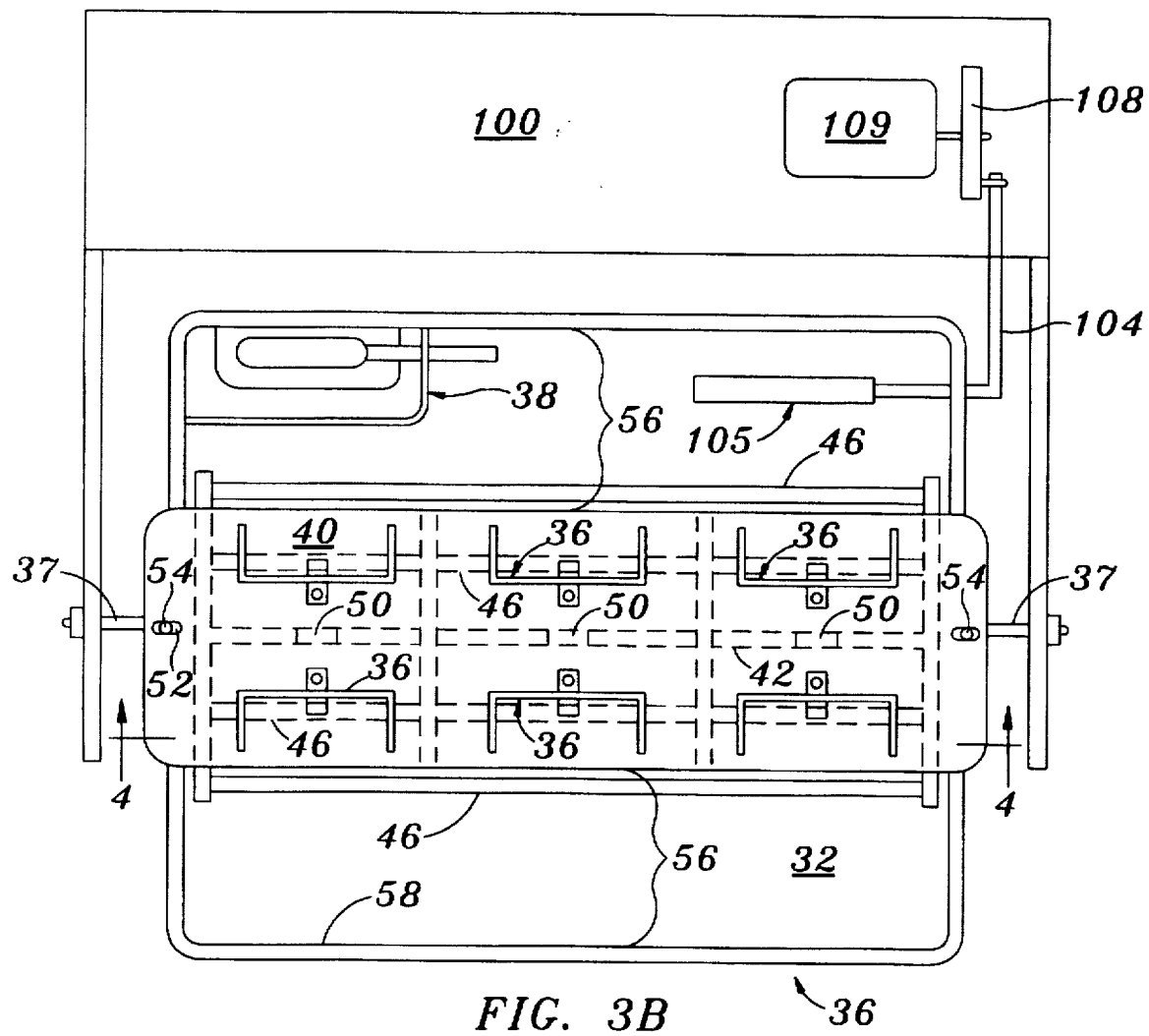
FIG. 3b is a plan view of another embodiment having a plate member attached to a rocking arm which oscillates the fluid in the bath.
Figure 5:
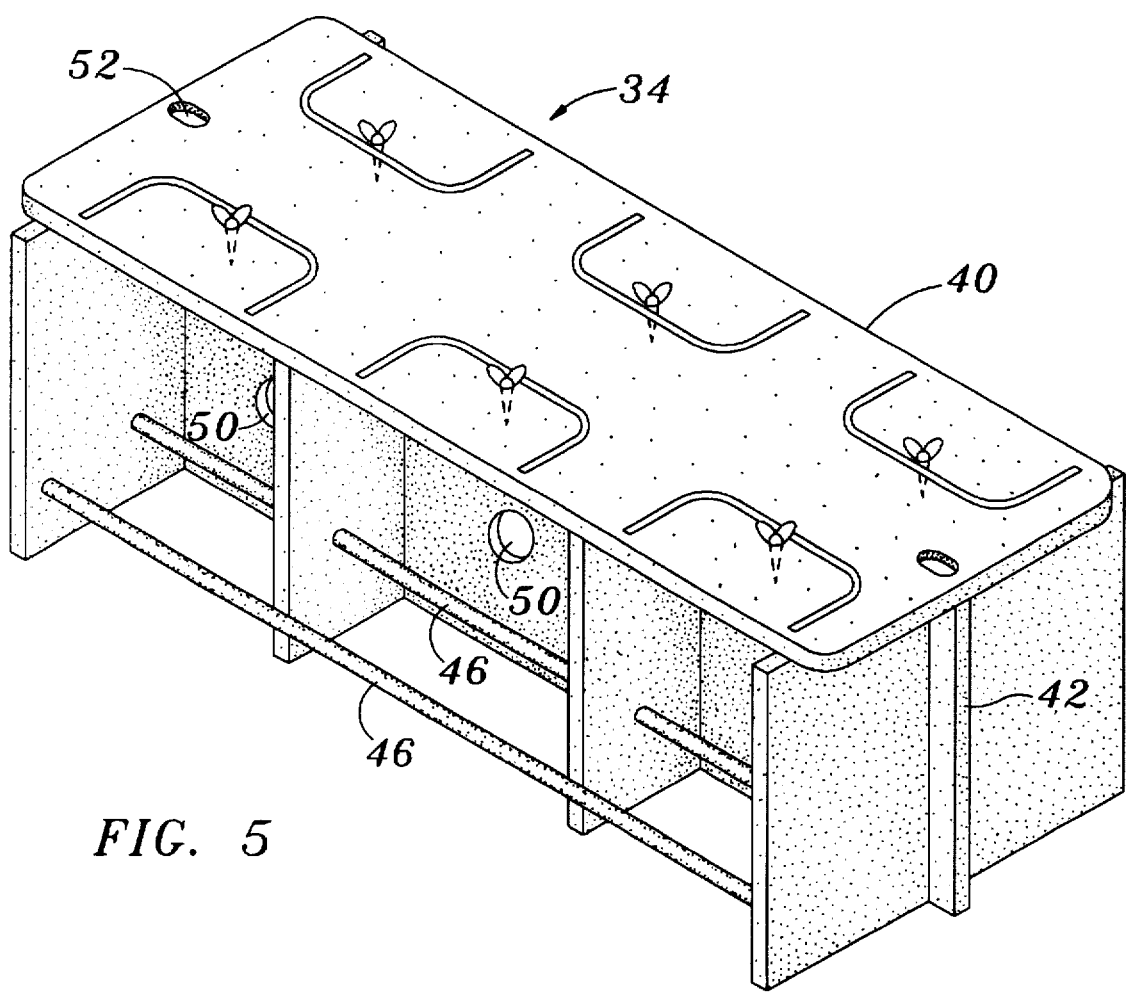
FIG. 5 is an isometric view of the holder shown in FIGS. 3 and 4.

FIG. 1 shows a typical plasma unit indicated generally at the reference character 10 which includes a relatively thick plastic pouch-like container 12 filled with the plasma. The pouch 12 typically will have at least one filling as well as one, or sometimes two outlet ports through which the plasma will flow after being thawed when the unit is used. One end of the plastic plasma container 12 is typically provided with a flange 24 having a hole 25 to enable the unit to be suspended overhead when administering the plasma to a patient. It is commonly accepted practice to try to maintain the outlet ports and various connector tubes in a completely sealed isolated environment so as to avoid contamination during the thawing process and until the moment at which the unit is to be used.

With reference to FIGS. 2–5, the fluid bath may take any of a number of forms and preferably includes a tub 32 through which thermostatically controlled fluid is circulated. To that end, the tub may be associated with a pump, a heating element and thermostat controls, indicated generally as being contained within a housing 38 associated with the tub 32 (see FIG. 3). The details of such pump and control mechanism are well known to those skilled in the art and require no further discussion.

A control terminal 100 is provided adjacent the tub 32, and controls the pump, heating element and oscillation of the tub 32 itself or fluid within the tub 32 as will be discussed below.

The tub 32 is mounted for rocking or pivotal movement and may be connected to an oscillating mechanism which agitates the fluid to thereby promote more rapid thawing. The oscillating mechanism may comprise a rocking arm 104 which may be pivoted by, for example, an eccentric wheel 108. The eccentric wheel 108 is rotated by a motor 109 or other suitable rotational means, and in turn causes the rocking arm 104 to rock or pivot the tub 32 about the tub support pins 37. The specific design of the oscillating mechanism maximizes on the pivoting efficiency of the entire system. Of course, the oscillating mechanism is not limited to the design shown in the drawings and described above, but may include any such mechanism as known by those of skill in the art. Examples of other mechanisms and methods to create oscillating fluid within the bath include the use of a moveable plate member(s) within a relatively stationary bath to create waves moving to and fro within the bath. The plate member could be linked to a cam or movable arm member which would create a mechanical movement of the plate 105 (see FIG. 3b). Another method would be to create jet fluid inputs from the fluid pump already associated with the system for controlling the fluid temperature. The jet system could be associated with a pulsing system for the pump itself or with an actuating valve, either of which would cause fluid to alternately jet into the tub and cause agitation of the fluid against the frozen bag.

In association with the present invention, a holder is provided to maintain the lower end of the bag (which contains the plasma or plasma pouch) below the fluid level of the bath while simultaneously holding the upper open end of the bag exposed to the atmosphere and other communication with the fluid. This holder may extend from across the tub and from above the tub as shown or may simply be an attachment of the bags to the side wall of the tub. As shown in the illustrated embodiment of FIGS. 2–5 the holder 34 includes an upper platform 40, a central dividing wall 42, a number of partitioning walls 44, and side walls 48. The upper platform 40 is longer than the dividing wall 42 and partitioning walls 44 so that the outer ends of the upper platform 40 extend outwardly beyond the side walls 48. The ends of the upper platform provide a convenient means by which the device may be mounted to the tub 32. In the embodiment shown, the outer ends of the upper platform 40 may be provided with openings 52 to receive registration pins 54 which may be secured to an extend upwardly from the tub 32.

The dividing wall 42 and partitioning walls 44 may be integrally formed with the upper platform 40 or otherwise connected to and suspended from the upper platform 40 as shown. In the preferred embodiment, the partitioning walls are arranged to partition the bath fluid in order to effectuate rapid thawing of each plasma bag, individually.

Figure 6:
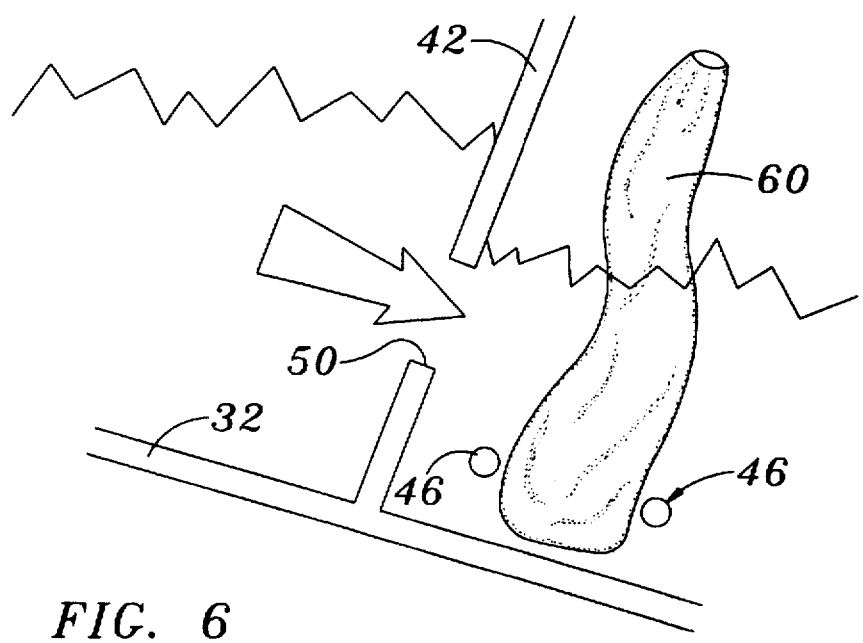
FIG. 6 is a schematic of the fluid concentration and resultant kneading action achieved by the instant invention.

In the illustrated embodiment of the invention, the central dividing wall 42 is provided with a plurality of apertures 50, to form a baffle plate, through which the fluid is adapted to pass as the fluid bath is oscillated or rocked. FIG. 6 provides a schematic illustration of the operation and function of the apertures 50 during operation of the instant invention. With reference to FIG. 6, as the bath 32 oscillates, the water level on one side of the central dividing wall 42 rises with respect to the other side of the dividing wall 42 thus creating a pressure differential on each side of the wall 42. Due to this pressure differential, the fluid will be forced through the aperture 50 in order to compensate for the difference in pressure. As the fluid passes through the aperture 50, a jet-like effect is created which massages or kneads an outer pouch support bag 60, or the plasma pouch directly if no outer bag is present, to enhance the thawing effect of the bath.

It will be understood by those of skill in the art that the aforementioned arrangement may be replaced with other fluid-jet producing baffles, or mechanisms previously described, which simulate the same fluid movement created kneading effect as described above. Such a jet will act much like a whirlpool jet to enhance thawing efficiency.

Associated with each partitioned section of the bag holder 34 are mounting means 36 which maintain each plasma bag in stable relative positions in the bath fluid. The mounting means 36 assure that the upper end of an open bag 60, or an upper end of the plasma pouch itself, will remain relatively still. In the case of the open bag type support 60, this mounting will allow the open end to be exposed to the atmosphere and at a location well above the fluid level so as not to be contaminated with any of the fluid. The pouch holder 34 preferably is arranged to provide adequate space 56 between a wall 58 of the tub and the side of the upper platform 40. The space 56 should be adequate for the user to insert and remove the bags from the holder with ease.

The system shown in FIGS. 2–5 is used by inserting the frozen plasma unit 10 into the pouch holder 34 directly or into the thin open ended, unsealed plastic bag (as shown in FIG. 6). With the plasma unit at the bottom of the bag 60 (if a bag holder is used), the pouch is then inserted into the bath, with its lower end containing the frozen plasma unit beneath the surface of the fluid.

The plasma unit 10 which is frozen and is buoyant, will be maintained fully submerged by the stabilizing members 46 positioned on the holder 34. The stabilizing members 46 function to maintain the bag or pouch in a submerged position and in a position adjacent the apertures 50 provided in the central dividing wall 42. Moreover, these stabilizing members 46 are designed to maintain the position of the bag or pouch even under the pressure of the water passing through the apertures 50 or the pressure of other jet producing means.

The foregoing illustrates but one of various possible configurations of holders and stabilizer/reaction members utilizing the present system. An alternate embodiment of a bag holder may be mounted directly to the bottom wall of a tub as by suction cups such as described in U.S Pat. No. 4,486,389.

It will also be understood that the foregoing description of the invention is intended merely to be illustrative thereof and that other modifications and embodiments may be apparent to those skilled in the art without departing from its spirit.

I claim:

1. A system for thawing a frozen plasma unit pouch comprising;
   a fluid bath adapted to hold a quantity of fluid;
   mounting means for supporting said pouch in a substantially submerged position with respect to said quantity of fluid when containing said frozen plasma unit pouch;
   means for varying a flow of the fluid in said fluid bath to create a kneading effect on the exterior of the frozen plasma unit to thereby reduce the thawing time of said frozen plasma unit,
   wherein said means for varying the flow of the fluid comprises a wall positioned in said fluid adjacent said pouch and an oscillating means for generating a differential in water depth on opposite sides of said wall, said wall comprising at least one aperture through which said fluid passes as a result of said differential to create said kneading effect.

2. The system as defined in claim 1, wherein said mounting means comprises an upper platform above the fluid level, and a fastening means for affixing said pouch to said upper platform in spaced relationship from the fluid level.

3. The system as defined in claim 1, wherein said mounting means comprises a stabilizing means submerged in said fluid for maintaining said pouch in a submerged position and adjacent said means for varying the flow of the fluid.

4. The system as defined in claim 3, wherein said stabilizing means comprises spaced rods adapted to received said pouch in a space between said spaced rods.

5. The system as defined in claim 1, wherein said fluid bath comprises sidewalls, the pouch being located with respect to one of the sidewalls so that there is a substantial space between said sidewall and said mounting means, said substantial space providing a region to facilitate insertion and removal of said pouch from said fluid bath.

6. The system as recited in claim 1, wherein said oscillating means comprises a mechanism which rocks said bath to and fro and oscillates said fluid within said bath.

7. The system as recited in claim 1, wherein said oscillating means comprises a movable plate member within said bath which moves to and fro within said fluid to cause oscillation of said fluid within said bath.

* * * * *